(12) United States Patent
Salandre

(10) Patent No.: US 11,103,881 B2
(45) Date of Patent: Aug. 31, 2021

(54) AIR VENT

(71) Applicant: Faurecia Interior Systems, Inc., Auburn Hills, MI (US)

(72) Inventor: Maxime Salandre, Rochester, MI (US)

(73) Assignee: Faurecia Interior Systems, Inc., Auburn Hills, MI (US)

( * ) Notice: Subject to any disclaimer, the term of this patent is extended or adjusted under 35 U.S.C. 154(b) by 411 days.

(21) Appl. No.: 16/052,756

(22) Filed: Aug. 2, 2018

(65) Prior Publication Data

US 2020/0038879 A1 Feb. 6, 2020

(51) Int. Cl.

| | |
|---|---|
| *B03C 3/017* | (2006.01) |
| *B03C 3/41* | (2006.01) |
| *B03C 3/06* | (2006.01) |
| *B03C 3/12* | (2006.01) |
| *B03C 3/64* | (2006.01) |
| *B03C 3/49* | (2006.01) |
| *B03C 3/47* | (2006.01) |
| *B60H 3/00* | (2006.01) |
| *B03C 3/66* | (2006.01) |

(52) U.S. Cl.
CPC ............... *B03C 3/017* (2013.01); *B03C 3/06* (2013.01); *B03C 3/12* (2013.01); *B03C 3/41* (2013.01); *B03C 3/47* (2013.01); *B03C 3/49* (2013.01); *B03C 3/64* (2013.01); *B03C 3/66* (2013.01); *B60H 3/0078* (2013.01); *B03C 2201/04* (2013.01); *B03C 2201/30* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 3,361,337 | A | * | 1/1968 | Hurst | H05H 1/00 315/111.91 |
| 3,699,387 | A | * | 10/1972 | Edwards | H01T 14/00 361/230 |
| 3,751,715 | A | * | 8/1973 | Edwards | H01T 23/00 361/230 |
| 5,334,347 | A | * | 8/1994 | Hollander | A61L 9/20 250/455.11 |
| 5,913,809 | A | * | 6/1999 | Erlichman | F02M 25/12 60/272 |
| 5,919,422 | A | * | 7/1999 | Yamanaka | A61L 2/232 422/121 |
| 5,993,738 | A | * | 11/1999 | Goswani | A61L 9/18 422/121 |
| 6,168,689 | B1 | * | 1/2001 | Park | B01D 53/323 204/164 |
| 6,504,308 | B1 | * | 1/2003 | Krichtafovitch | H01J 49/04 250/423 R |
| 6,544,485 | B1 | * | 4/2003 | Taylor | A61L 9/015 422/121 |
| 6,589,489 | B2 | * | 7/2003 | Morrow | A61L 9/015 422/186.3 |

(Continued)

FOREIGN PATENT DOCUMENTS

| | | | | | |
|---|---|---|---|---|---|
| EP | 2762170 B1 | * | 12/2015 | ........... | B01D 53/007 |
| JP | 60002832 A | * | 1/1985 | ............... | F24F 3/166 |
| WO | WO-2017143255 A1 | * | 8/2017 | ............... | B03C 3/47 |

*Primary Examiner* — Christopher P Jones
*Assistant Examiner* — Sonji Turner
(74) *Attorney, Agent, or Firm* — Barnes & Thornburg LLP

(57) ABSTRACT

An air vent system includes a conduit for airflow. A stream of air is moved through the conduit.

9 Claims, 4 Drawing Sheets

(56) References Cited

U.S. PATENT DOCUMENTS

| | | | | |
|---|---|---|---|---|
| 6,668,563 B2* | 12/2003 | Mirowsky | | B64D 13/00 |
| | | | | 315/111.91 |
| 6,685,803 B2* | 2/2004 | Lazarovich | | B01D 53/326 |
| | | | | 204/164 |
| 6,834,492 B2 | 12/2004 | Hruby | | |
| 7,037,468 B2* | 5/2006 | Hammerstrom | | A61L 2/14 |
| | | | | 422/22 |
| 7,091,481 B2* | 8/2006 | Miller | | G01N 27/624 |
| | | | | 250/286 |
| 7,274,015 B2* | 9/2007 | Miller | | G01N 21/68 |
| | | | | 250/286 |
| 7,279,680 B2* | 10/2007 | Miller | | G01N 27/624 |
| | | | | 250/286 |
| 7,311,762 B2* | 12/2007 | Taylor | | B03C 3/32 |
| | | | | 422/186.04 |
| 7,380,756 B1* | 6/2008 | Enloe | | H05H 1/2406 |
| | | | | 244/175 |
| 7,517,504 B2* | 4/2009 | Taylor | | A61L 9/015 |
| | | | | 422/186.04 |
| 7,553,353 B2* | 6/2009 | Lepage | | A61L 9/16 |
| | | | | 361/235 |
| 7,594,959 B2* | 9/2009 | Nutsos | | B03C 3/155 |
| | | | | 55/DIG. 39 |
| 7,595,030 B2* | 9/2009 | Joannou | | B03C 3/12 |
| | | | | 422/121 |
| 8,003,058 B2* | 8/2011 | Bergeron | | B01D 53/007 |
| | | | | 422/186.04 |
| 8,205,600 B2* | 6/2012 | Hammer | | F02M 25/12 |
| | | | | 123/539 |
| 8,211,374 B2* | 7/2012 | Hallam | | B01D 46/50 |
| | | | | 422/186.07 |
| 8,400,751 B2* | 3/2013 | Tanaka | | B64C 21/00 |
| | | | | 361/230 |
| 8,529,830 B2* | 9/2013 | Zhou | | B03C 3/68 |
| | | | | 422/4 |
| 8,559,158 B2* | 10/2013 | Tanaka | | B64C 23/005 |
| | | | | 361/230 |
| 9,005,531 B2* | 4/2015 | Mole | | H05H 1/2406 |
| | | | | 422/121 |
| 9,145,874 B2 | 9/2015 | Slough | | |
| 9,216,233 B2* | 12/2015 | Ota | | B03C 3/368 |
| 9,282,623 B2* | 3/2016 | Roy | | H05H 1/2406 |
| 9,381,267 B2* | 7/2016 | Tsui | | A61L 9/22 |
| 9,657,725 B2 | 5/2017 | Berl | | |
| 9,839,714 B2* | 12/2017 | Waddell | | B03C 3/41 |
| 10,111,978 B2* | 10/2018 | Waddell | | F02M 35/0205 |
| 2001/0023589 A1* | 9/2001 | Tamura | | B01D 53/32 |
| | | | | 60/747 |
| 2002/0068012 A1* | 6/2002 | Platt, Jr. | | A61L 2/14 |
| | | | | 422/22 |
| 2002/0168305 A1* | 11/2002 | Morrow | | A61L 9/015 |
| | | | | 422/186.3 |
| 2003/0070913 A1* | 4/2003 | Miller | | H01J 49/105 |
| | | | | 204/192.1 |
| 2003/0206837 A1* | 11/2003 | Taylor | | C01B 13/115 |
| | | | | 422/186 |
| 2003/0206839 A1* | 11/2003 | Taylor | | C01B 13/115 |
| | | | | 422/186.04 |
| 2003/0206840 A1* | 11/2003 | Taylor | | B01D 53/32 |
| | | | | 422/186.04 |
| 2004/0251909 A1* | 12/2004 | Taylor | | C01B 13/11 |
| | | | | 324/509 |
| 2005/0118079 A1* | 6/2005 | Muroi | | B01D 53/32 |
| | | | | 422/186.3 |
| 2005/0121607 A1* | 6/2005 | Miller | | G01N 27/624 |
| | | | | 250/287 |
| 2005/0142045 A1* | 6/2005 | Yuen | | A61L 9/20 |
| | | | | 422/186.3 |
| 2005/0163669 A1* | 7/2005 | Taylor | | B01D 53/32 |
| | | | | 422/121 |
| 2005/0238551 A1* | 10/2005 | Snyder | | A61L 9/205 |
| | | | | 422/186.3 |
| 2006/0018807 A1* | 1/2006 | Taylor | | H01J 61/302 |
| | | | | 422/186.3 |
| 2006/0018808 A1* | 1/2006 | Taylor | | B03C 3/74 |
| | | | | 422/186.04 |
| 2006/0018810 A1* | 1/2006 | Taylor | | B03C 3/68 |
| | | | | 422/186.04 |
| 2006/0018811 A1* | 1/2006 | Taylor | | B03C 3/86 |
| | | | | 422/186.04 |
| 2006/0021509 A1* | 2/2006 | Taylor | | B03C 3/68 |
| | | | | 96/83 |
| 2006/0159594 A1* | 7/2006 | Parker | | F24F 3/16 |
| | | | | 422/121 |
| 2006/0237669 A1* | 10/2006 | Miller | | G01N 27/624 |
| | | | | 250/504 R |
| 2007/0009406 A1* | 1/2007 | Taylor | | B03C 3/32 |
| | | | | 422/186.04 |
| 2007/0247076 A1* | 10/2007 | Fujioka | | H05H 1/2406 |
| | | | | 315/111.21 |
| 2007/0253860 A1* | 11/2007 | Schroder | | A61L 9/205 |
| | | | | 422/4 |
| 2008/0156981 A1* | 7/2008 | Miller | | G01N 27/624 |
| | | | | 250/287 |
| 2008/0170971 A1* | 7/2008 | Bergeron | | B03C 3/12 |
| | | | | 422/171 |
| 2008/0193326 A1* | 8/2008 | Mole | | B01D 53/66 |
| | | | | 422/2 |
| 2009/0010801 A1* | 1/2009 | Murphy | | F24F 3/166 |
| | | | | 422/4 |
| 2009/0071328 A1* | 3/2009 | Dunn | | B03C 3/09 |
| | | | | 95/62 |
| 2009/0202397 A1* | 8/2009 | Parker | | B03C 3/41 |
| | | | | 422/121 |
| 2010/0089234 A1* | 4/2010 | Khoury | | B03C 3/41 |
| | | | | 95/81 |
| 2014/0294681 A1* | 10/2014 | Mole | | A61L 9/22 |
| | | | | 422/121 |
| 2016/0083119 A1 | 3/2016 | Davidson | | |
| 2017/0056543 A1* | 3/2017 | Mole | | H05H 1/2406 |

\* cited by examiner

AIR VENT

BACKGROUND

The present disclosure relates to ventilation systems for use in a vehicle. More particularly, the present disclosure relates to an air vent for a vehicle.

SUMMARY

According to the present disclosure, an air vent system includes a conduit for airflow from an inlet of the conduit to an outlet of the conduit. The air vent system may be used in a vehicle or any other suitable application.

In illustrative embodiments, the air vent system further includes an ionic airflow generator positioned within the conduit, an ultraviolet light generator positioned within the conduit between the ionic airflow generator and the outlet, and an electrostatic trap positioned within the conduit between the ionic airflow generator and the outlet. The ionic airflow generator includes a first electrode and a second electrode. The first electrode and the second electrode generate a plasma when coupled to an alternating current, and the plasma induces airflow through the conduit from the inlet to the outlet. The ultraviolet light generator generates ultraviolet light within the conduit that is incident on the airflow, and the electrostatic trap generates an electric field within the conduit that acts upon the airflow.

In illustrative embodiments, the ionic airflow generator further includes a dielectric and an insulating substrate. The first electrode and the second electrode are separated by the dielectric and positioned apart along an axis of the conduit. The first electrode is exposed to the airflow, and the second electrode is encapsulated in the insulating substrate. In illustrative embodiments, the first electrode may be a tungsten wire and the second electrode may be a copper tape. In illustrative embodiments, the dielectric may be a glass sheet and the insulating substrate may be an epoxy resin.

In illustrative embodiments, the electrostatic trap may include multiple charged tubes in a spaced apart relation to one another and positioned within the conduit. In illustrative embodiments, the electrostatic trap may include a charged grid positioned within the conduit.

In illustrative embodiments, the ultraviolet light generator may generate light having a wavelength between 240 nanometers and 350 nanometers. In illustrative embodiments, the ultraviolet light generator may generate light having a wavelength of 311 nanometers.

In illustrative embodiments, the alternating current may have a frequency between 1 kHz and 6 kHz. In illustrative embodiments, the alternating current may have a voltage between 13 kV and 30 kV.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Figure 1:
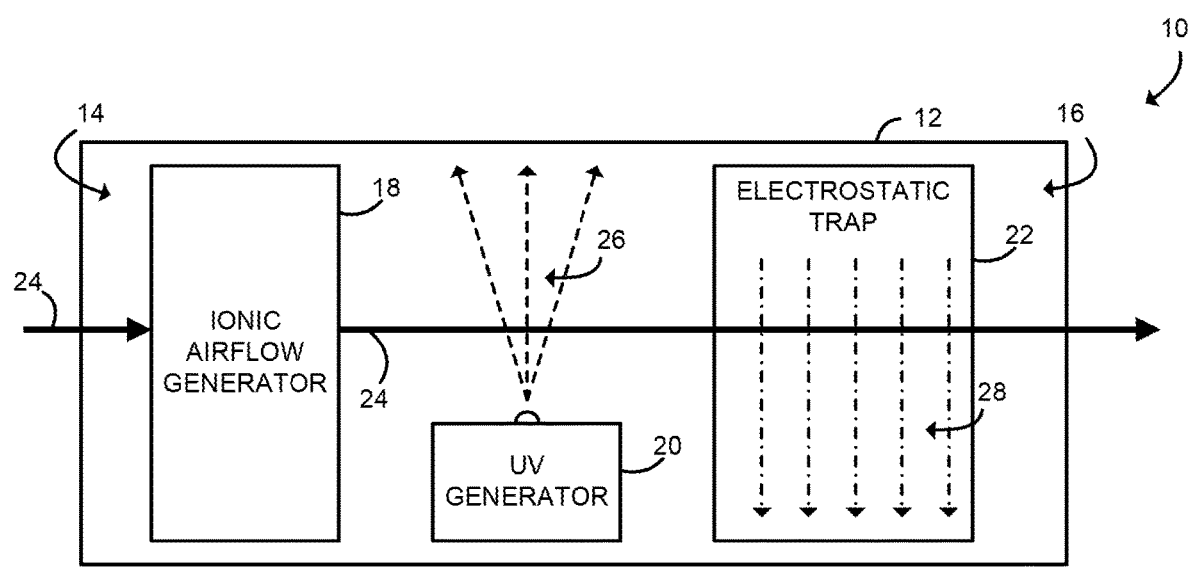
FIG. 1 is a diagrammatic view of an electrohydrodynamic air vent system in accordance with the present disclosure suggesting that the air vent system includes an ionic flow generator, an ultraviolet light generator, and an electrostatic trap.

An electrohydrodynamic air vent system 10 in accordance with the present disclosure is shown in FIG. 1. As shown, the air vent system 10 includes a conduit 12 adapted for the passage of air between an inlet 14 and an outlet 16. The conduit may be made of any material appropriate for conducting the passage of air, and similarly may have a cross section of circular, rectangular, or any other shape adapted for the conducting the passage of air. As shown, the air vent system 10 further includes an ionic airflow generator 18, an ultraviolet light generator 20, and an electrostatic trap 22 all positioned within the conduit 12. As described further below, in use, the ionic airflow generator 18 generates an airflow 24 that passes from the inlet 14 to the outlet 16, through the ultraviolet light generator 20 and through the electrostatic trap 22. The ultraviolet light generator 20 generates ultraviolet light 26 that shines through the airflow 24, inhibiting the generation of ozone within the airflow 24. The electrostatic trap 22 creates an electric field 28 that removes charged particles from the airflow 24.

Accordingly, the air vent system 10 generates a flow of air that may be used to ventilate the interior cabin of a vehicle such as a car. Unlike traditional fans and other mechanical air vent systems, the disclosed air vent system 10 includes no moving parts, and thus the air vent system 10 as disclosed herein may have reduced noise and increased longevity as compared to traditional air vent systems. The air vent system 10 may require limited assembly and thus may reduce manufacturing costs. Additionally, the air vent system 10 may be flexibly packaged and located throughout the vehicle cabin and thus may improve cabin ventilation, particularly for remote occupants.

Although illustrated in FIG. 1 as including an ionic air generator 18, an ultraviolet light generator 20, and an electrostatic trap 22, it should be understood that in other embodiments the air vent system 10 may include a different combination and/or arrangement of those components. For example, in some embodiments, the air vent system 10 may include an ionic air generator 18 and an ultraviolet light generator 20; an ionic air generator 18 and an electrostatic trap 22; and/or an ionic air generator without the ultraviolet light generator 20 or the electrostatic trap 22. Additionally or alternatively, although illustrated as treating the airflow 24 with the ultraviolet light generator 20 before the airflow 24 enters the electrostatic trap 22, it should be understood that in some embodiments the airflow may enter the electrostatic trap 22 before being treated by the ultraviolet light generator 20.

Figure 2:
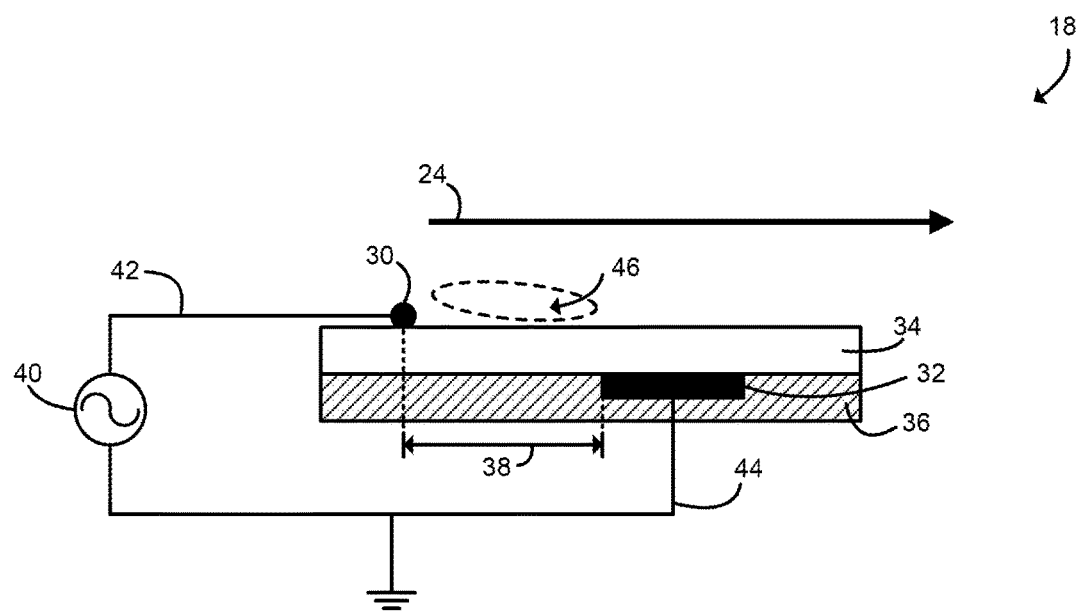
FIG. 2 is a diagrammatic view of at least one potential embodiment of the ionic airflow generator of the air vent system of FIG. 1.

The ionic airflow generator 18, as shown in FIG. 2, includes a pair of electrodes 30, 32 separated by a dielectric 34. The electrode 30 may be referred to as the active electrode 30, and the electrode 32 may be referred to as the ground electrode 32. The electrode 30 is illustratively a tungsten wire attached to a top surface of the dielectric 34 and exposed to air, for example, air within the conduit 12 of the air vent system 10. The electrode 32 is illustratively copper tape attached to a bottom surface of the dielectric 34. The electrode 32 is encapsulated by an insulating substrate 36 and is thus not exposed to air. The electrodes 30, 32 are separated by a distance 38 in the direction of the generated airflow 24. For example, the electrodes 30, 32 may be positioned along an axis of the conduit 12 to cause the airflow 24 to pass through the conduit 12. Although illustrated as a wire and a copper plate, it should be understood that in other embodiments the electrodes 30, 32 may have different shapes and/or be constructed from different materials. Similarly, the dielectric 34 is illustratively a glass plate that is two millimeters thick, but in other embodiments may be a different dielectric material, such as a polymer dielectric, and/or a different thickness. The insulating substrate 36 is illustratively epoxy resin but in other embodiments may be a different insulating material.

The electrodes 30, 32 are connected to an alternating electrical current source 40 by a supply line 42 and a ground line 44, respectively. The alternating electrical current source 40 may operate at relatively high frequencies and/or voltages. For example, in some embodiments the alternating current source 40 may operate at frequencies between 1 kHz and 6 KHz. In some embodiments, the alternating current source 40 may operate at voltages between 13 kV and 30 kV. When an alternating current is applied to the electrodes 30, 32, a plasma 46 is generated over the dielectric 34 between the active electrode 30 and the ground electrode 32. The plasma 46 induces the airflow 24, which travels from the active electrode 30 toward the ground electrode 32 and then away from the ionic airflow generator 18, for example through the conduit 12 of the air flow system 10. The airflow 24 may be mostly neutral air molecules, although the airflow 24 may include ions from the plasma 46 and/or other charged particles.

Referring back to FIG. 1, the airflow 24 flows through the conduit 12 past the ultraviolet light generator 20, through the ultraviolet light 26. The ultraviolet light generator 20 may be embodied as any lamp, light emitting diode (LED), laser, or other device that emits the ultraviolet light 26. The ultraviolet light 26 prevents the formation of ozone molecules in the airflow 24. For example, the ultraviolet light 26 may change the oxidation state of air molecules in the airflow 24, that is, by adding enough energy to atoms of the airflow 24 to prevent wild electronic orbital jump at the quantum level. To prevent ozone formation, the ultraviolet light 26 may have a wavelength of between 240 and 350 nanometers, and may preferably have a wavelength of 311 nanometers. The conduit 12 may be opaque or otherwise prevent the ultraviolet light 26 from leaving the air vent system 10. Preventing ozone formation may improve the safety of the airflow 24 for occupants in a vehicle cabin. For example, after passing through the ultraviolet light 26, the airflow 24 may have an ozone concentration of less than forty parts per billion (ppb).

Figure 3:
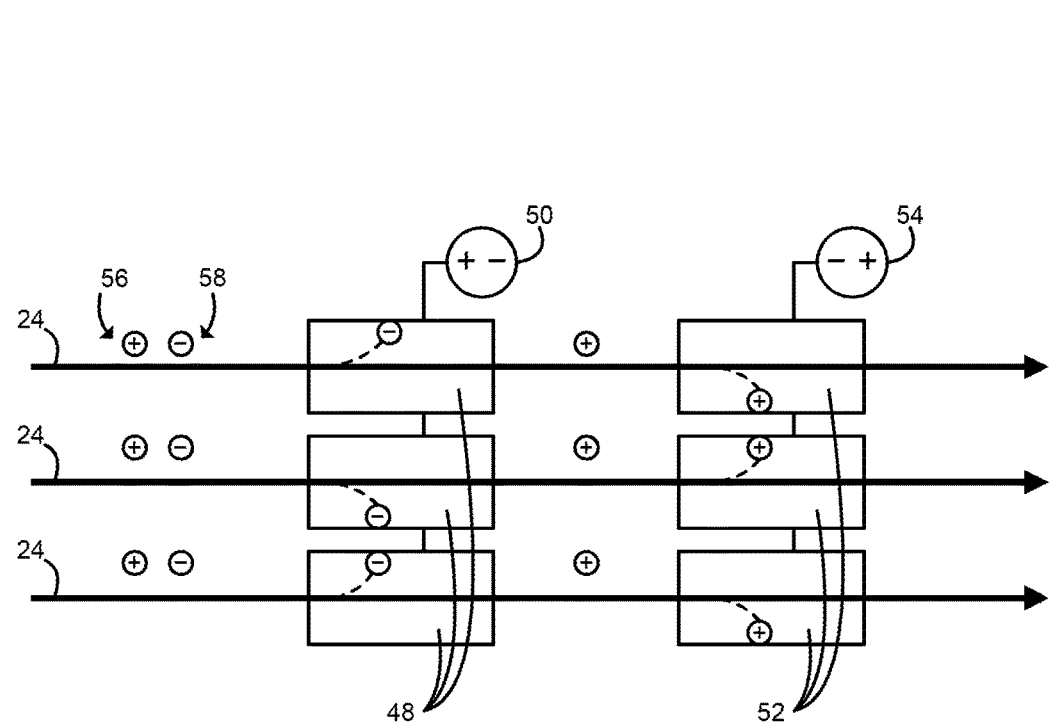
FIG. 3 is a side view of at least one potential embodiment of the electrostatic trap of the air vent system of FIG. 1.
Figure 4:
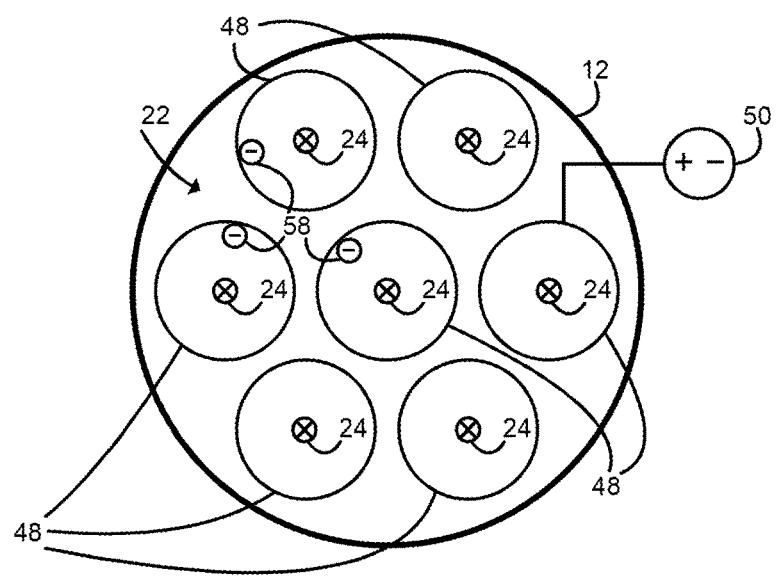
FIG. 4 is a cross-sectional view of the electrostatic trap of FIG. 3.

Referring now to FIGS. 3 and 4, one potential embodiment of the electrostatic trap 22 is shown. Illustratively, the electrostatic trap 22 includes multiple tubes 48, 52 positioned within the conduit 12 of the air vent system 10. Each tube 48, 52 may be constructed of copper or another conductive material. Each of the tubes 48, 52 is electrostatically charged. For example, in the illustrative embodiment, the tubes 48 are connected to a positive voltage source 50, and the tubes 52 are connected to a negative voltage source 54. The tubes 48, 52 thus generate an electric field 28 as described above.

As best shown in FIG. 3, the airflow 24 may include charged particles 56, 58. As described above, the charged particles 56, 58 may include ions generated by the ionic airflow generator 18 and/or other charged particles carried along by the airflow 24. As the airflow 24, including the charged particles 56, 58, passes through the electrostatic trap 22, negatively charged particles 58 are attracted to the positively charged tubes 48, and positively charged particles 56 are attracted to the negatively charged tubes 52. The charged particles 58, 56 may be trapped against the respective tubes 48, 52 by electrostatic forces and thus removed from the airflow 24. Removing the charged particles from the airflow 24 may improve the safety and/or convenience of the airflow 24 for occupants in a vehicle cabin, for example by reducing potential static electricity discharges experienced by the occupants. Similarly, removing the charged particles from the airflow 24 may protect electronic equipment from experiencing damage due to static electricity discharges. Additionally or alternatively, removing the charged particles from the airflow 24 may reduce dust, microbes, and/or odors carried by the airflow 24.

Figure 5:
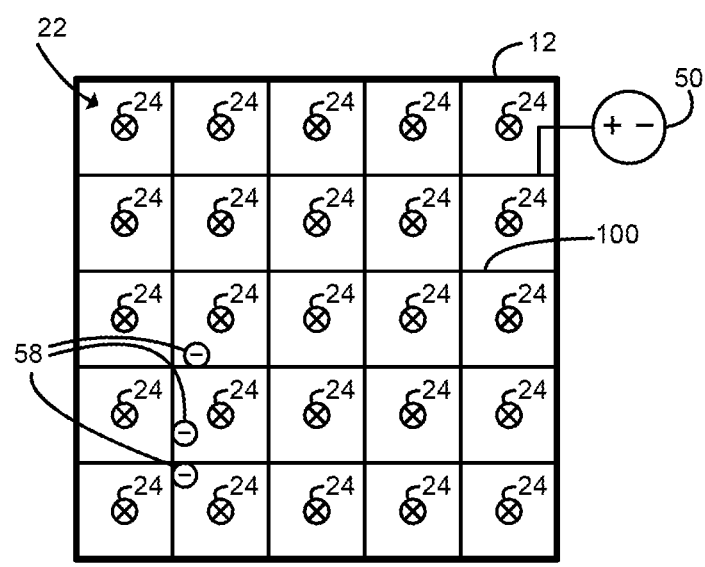
FIG. 5 is a cross-sectional view of another potential embodiment of the electrostatic trap of the air vent system of FIG. 1.

Although illustrated in FIGS. 3 and 4 as multiple round tubes arranged within the conduit 12 in a circular pattern, it should be understood that in other embodiments the electrostatic trap 22 may include any other arrangement of charged surfaces that extend into the airflow 24. For example, referring now to FIG. 5, in some embodiments the electrostatic trap 22 may include one or more electrically charged grids 100 positioned within the conduit 12. Similar to the tubes 48, 52, the grids 100 attract charged particles 56, 58 and remove the charged particles 56, 58 from the airflow 24. Although illustrated in FIG. 5 as including a positively charged grid 100 that attracts negatively charged particles 58, it should be understood that the electrostatic trap 22 may include multiple grids 100 with alternative charges (i.e., both positively and negatively charged grids 100) to remove positively charged particles 58 and negatively charged particles 58 from the airflow 24.

Figure 6:
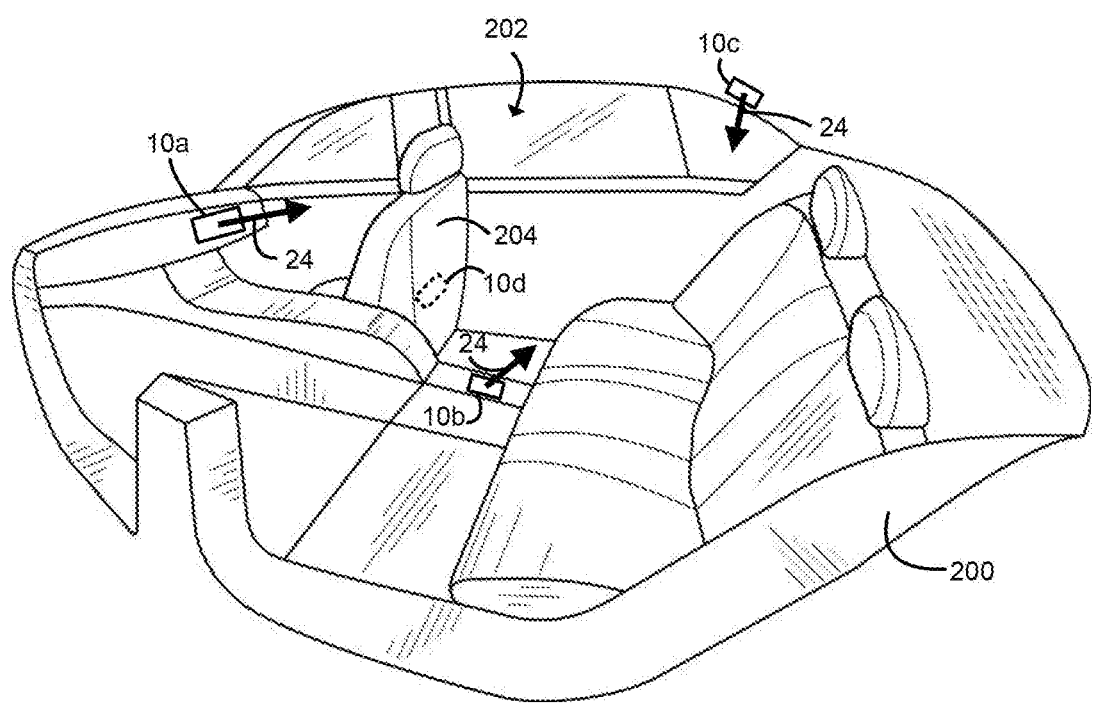
FIG. 6 is a diagrammatic view of a vehicle suggesting that the vehicle includes multiple air vent systems in accordance with the present disclosure.

Referring now to FIG. 6, an illustrative vehicle 200 with an interior cabin 202 is shown. As shown, multiple air vent systems 10 may be positioned throughout the cabin 202. Each air vent system 10 provides point-of-use airflow generation, and thus may be positioned nearby a vehicle occupant. For example, in the illustrative embodiment the air vent system 10a is positioned within the vehicle dashboard, the air vent system 10b is positioned in a rear seat console, and the air vent system 10c is positioned within the vehicle headliner. In addition to interior cabin 202 ventilation, the air vent system 10 may be used for other purposes, including cooling embedded or integrated electronics within the vehicle. For example, as illustrated in FIG. 6, the air vent system 10d is positioned within a seat 204 of the vehicle 200, for example to provide cooling for an integrated electronic control unit (ECU) located within the seat 204. Of course, in other embodiments different numbers and/or arrangements of the air vent system 10 may be included in the vehicle 200.

The following numbered clauses include embodiments that are contemplated and non-limiting:

Clause 1. An air vent system comprising a conduit for airflow from an inlet of the conduit to an outlet of the conduit; and an ionic airflow generator positioned within the conduit, wherein the ionic airflow generator comprises a first electrode and a second electrode, and wherein the first electrode and the second electrode generate a plasma when coupled to an alternating current, and wherein the plasma induces the airflow through the conduit from the inlet to the outlet.

Clause 2. The system of clause 1, any other clause, or combination of clauses, wherein the ionic airflow generator further comprises a dielectric and an insulating substrate;

the first electrode and the second electrode are separated by the dielectric and positioned apart along an axis of the conduit;

the first electrode is exposed to the airflow; and the second electrode is encapsulated in the insulating substrate.

Clause 3. The system of clause 2, any other clause, or combination of clauses, wherein the first electrode comprises a tungsten wire and the second electrode comprises a copper tape.

Clause 4. The system of clause 3, any other clause, or combination of clauses, wherein the dielectric comprises a glass sheet and the insulating substrate comprises an epoxy resin.

Clause 5. The system of clause 4, any other clause, or combination of clauses, further comprising an ultraviolet light generator positioned within the conduit between the ionic airflow generator and the outlet that generates ultraviolet light within the conduit that is incident on the airflow.

Clause 6. The system of clause 5, any other clause, or combination of clauses, wherein the ultraviolet light generator generates light having a wavelength between 240 nanometers and 350 nanometers.

Clause 7. The system of clause 5, any other clause, or combination of clauses, wherein the ultraviolet light generator generates light having a wavelength of 311 nanometers.

Clause 8. The system of clause 7, any other clause, or combination of clauses, further comprising an electrostatic trap positioned within the conduit between the ionic airflow generator and the outlet, wherein the electrostatic trap generates an electric field within the conduit that acts upon the airflow.

Clause 9. The system of clause 8, any other clause, or combination of clauses, wherein the electrostatic trap comprises a plurality of charged tubes in a spaced apart relation to one another and positioned within the conduit.

Clause 10. The system of clause 8, any other clause, or combination of clauses, wherein the electrostatic trap comprises a charged grid positioned within the conduit.

Clause 11. The system of clause 10, any other clause, or combination of clauses, wherein the alternating current has a frequency between 1 kHz and 6 kHz.

Clause 12. The system of clause 11, any other clause, or combination of clauses, wherein the alternating current has a voltage between 13 kV and 30 kV.

The invention claimed is:

1. An air vent system comprising:
   a conduit for airflow from an inlet of the conduit to an outlet of the conduit;
   an ionic airflow generator positioned within the conduit, wherein the ionic airflow generator comprises a first electrode and a second electrode, and wherein the first electrode and the second electrode generate a plasma when coupled to an alternating current, and wherein the plasma induces the airflow through the conduit from the inlet to the outlet;
   an ultraviolet light generator positioned within the conduit between the ionic airflow generator and the outlet that generates ultraviolet light within the conduit that is incident on the airflow; and
   an electrostatic trap positioned within the conduit between the ionic airflow generator and the outlet, wherein the electrostatic trap generates a static electric field within the conduit that acts upon the airflow;
   wherein the ionic airflow generator further comprises a dielectric and an insulating substrate, the first electrode and the second electrode are separated by the dielectric and positioned apart along an axis of the conduit, the first electrode is exposed to the airflow, and the second electrode is encapsulated in the insulating substrate;
   wherein the first electrode is positioned closer to the inlet of the conduit than the second electrode.

2. The air vent system of claim 1, wherein the first electrode comprises a tungsten wire and the second electrode comprises a copper tape.

3. The air vent system of claim 1, wherein the dielectric comprises a glass sheet and the insulating substrate comprises an epoxy resin.

4. The air vent system of claim 1, wherein the electrostatic trap comprises a plurality of charged tubes in a spaced apart relation to one another and positioned within the conduit.

5. The air vent system of claim 1, wherein the electrostatic trap comprises a charged grid positioned within the conduit.

6. The air vent system of claim 1, wherein the ultraviolet light generator generates light having a wavelength between about 240 nanometers and about 350 nanometers.

7. The air vent system of claim 1, wherein the ultraviolet light generator generates light having a wavelength of about 311 nanometers.

8. The air vent system of claim 1, wherein the alternating current has a frequency between about 1 kHz and about 6 kHz.

9. The air vent system of claim 1, wherein the alternating current has a voltage between about 13 kV and about 30 kV.

* * * * *